United States Patent [19]

Suzuki

[11] Patent Number: 5,936,772
[45] Date of Patent: Aug. 10, 1999

[54] LIGHT SOURCE OPTICAL SYSTEM FOR ENDOSCOPES

[75] Inventor: Takayuki Suzuki, Hachioji, Japan

[73] Assignee: Oympus Optical Co., Ltd., Tokyo, Japan

[21] Appl. No.: 09/031,052

[22] Filed: Feb. 26, 1998

[30] Foreign Application Priority Data

Apr. 16, 1997 [JP] Japan .................................... 9-099315

[51] Int. Cl.$^6$ .............................. G02B 27/10; A61B 1/00; A61B 17/36
[52] U.S. Cl. .............................. 359/627; 600/101; 606/16
[58] Field of Search ........................... 359/627; 600/101; 606/16

[56] References Cited

U.S. PATENT DOCUMENTS 4,474,419  10/1984  Konoshima ............................. 339/147
5,335,648   8/1994  Kozawa et al. ............................ 128/6

FOREIGN PATENT DOCUMENTS 1-135408  9/1989  Japan .

*Primary Examiner*—Georgia Epps
*Assistant Examiner*—Michael A Lucas
*Attorney, Agent, or Firm*—Pillsbury Madison & Sutro LLP

[57] ABSTRACT

A light source optical system for endoscopes includes an elliptical condensing mirror projecting a bright spot of the light-emitting section of a lamp and a relay optical system transmitting the projected image of the bright spot to the entrance end face of a light guide. The elliptical condensing mirror is designed to satisfy the following condition:

2.0 mm<F<16.0 mm where F is the focal length of the elliptical condensing mirror, which is expressed by $F=\beta^2/(2\alpha)$ where (the major axis of an ellipse)/$2=\alpha$ and (the minor axis of the ellipse)/$2=\beta$. In this way, a light beam from the light-emitting section can be efficiently condensed on the entrance end face of the light guide and the entire light source optical system can be constructed to be compact.

14 Claims, 4 Drawing Sheets

B TRANSMISSION FILTER

G TRANSMISSION FILTER

R TRANSMISSION FILTER

LIGHT SOURCE OPTICAL SYSTEM FOR ENDOSCOPES

BACKGROUND OF THE INVENTION

1. Field of the Invention

This invention relates to a light source optical system for endoscopes, particularly having an elliptical condensing mirror projecting a bright spot of the light-emitting section of a lamp and a relay optical system transmitting the projected image of the bright spot to the entrance end face of a light guide.

2. Description of Related Art

In general, observation with an endoscope needs an illumination system including, at least, a light source supplying light to illuminate a subject for observation and a light guide transmitting the light emitted from the light source to the distal end of the endoscope. The light source is constructed with a discharge lamp giving out intense light, such as a xenon lamp or a metal halide lamp, and a condensing optical system efficiently collecting the light emitted from this lamp on the entrance end face of the light guide. As an example, a light source optical system set forth in Japanese Utility Model Preliminary Publication No. Hei 1-135408 is known. This optical system includes an elliptical condensing mirror placed so that the center of the light-emitting section of the discharge lamp is located at the primary focal point thereof, and first and second condenser lenses situated behind the secondary focal point of the elliptical condensing mirror to collect light. The optical system has the function that the bright spot of the light-emitting section is projected in a space by the elliptical condensing mirror and the projected image is transmitted to the entrance end face of the light guide by the condenser lenses.

Recently, by the widespread use of endoscopes, their applications to observations have been diversified, and endoscope observation systems with high versatility which can accommodate such applications have been in demand. In keeping with this, the improvements of an observer's work efficiency and of ease with which the observer handles apparatuses have come into big problems to be solved. Endoscopes are available in different kinds, such as an endoscope of relatively large diameter for observing and treating the stomach or intestines and an endoscope of extremely small diameter for observing the interior of a blood vessel. Such endoscopes require light source apparatuses to supply illumination light with brightness sufficient for such observations. In view of the observer's work efficiency, it is imperative to provide a light source apparatus with lightweight and compact design such that it is easy to carry and does not occupy much space when placed.

In the light source optical system of this type, on the other hand, the light-emitting section of the lamp has a light-emitting area with a certain size, and thus a question arises as to how efficiently the light from the lamp is collected on the entrance end face of the light guide. Specifically, the question is due to not only how the focal length of the elliptical condensing mirror is determined with respect to the light-emitting section having a certain dimension along the optical axis, but also how the effective aperture diameter of the elliptical condensing mirror having the determined focal length is determined to optimize the brightness of the light collected on the end face of the light guide and the size of the light beam.

SUMMARY OF THE INVENTION

It is, therefore, an object of the present invention to provide a light source optical system for endoscopes in which not only can light-collecting efficiency be improved with respect to the end face of a fine light guide, but also various filters are easily introduced and compact design can be achieved.

In order to accomplish this object, the light source optical system for endoscopes according to the present invention includes an elliptical condensing mirror projecting a bright spot of the light-emitting section of a lamp and a relay optical system transmitting the projected image of the bright spot to the entrance end face of a light guide. The elliptical condensing mirror is designed to satisfy the following condition:

$$2.0 \text{ mm} < F < 16.0 \text{ mm} \tag{1}$$

where F is the focal length of the elliptical condensing mirror, which is expressed by $F=\beta^2/(2\alpha)$ where (the major axis of an ellipse)$/2=\alpha$ and (the minor axis of the ellipse)$/2=\beta$.

Further, according to the present invention, a plane mirror is interposed on an optical path between the elliptical condensing mirror and the relay optical system so that the optical path is bent at an angle P satisfying the following condition:

$$30° < P < 120 \tag{2}$$

Still further, according to the present invention, the plane mirror is located so as to satisfy the following condition:

$$|L/\tan \theta| \leq 5.5 \tag{3}$$

where L is a distance from the secondary focal point of the elliptical condensing mirror to the plane mirror and $\theta$ is the maximum angle of incidence of a ray reflected by the elliptical condensing mirror on the secondary focal point.

This and other objects as well as the features and advantages of the present invention will become apparent from the following detailed description of the preferred embodiments when taken in conjunction with the accompanying drawings.

DETAILED DESCRIPTION OF THE PREFERRED EMBODIMENTS

Figure 1:
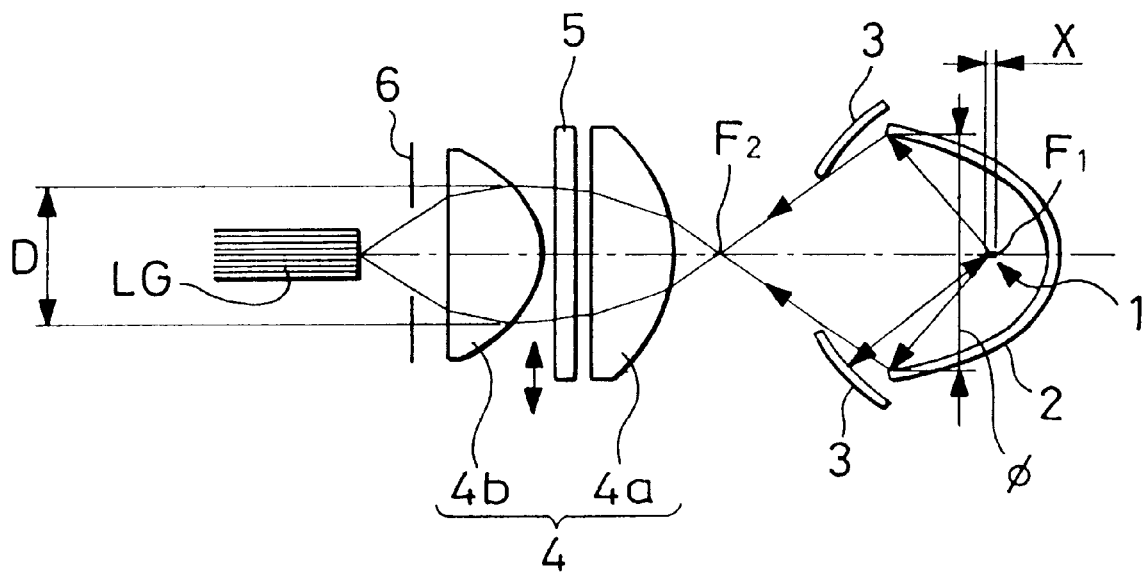
FIG. 1 is a view showing the arrangement of a first embodiment of the light source optical system for endoscopes according to the present invention.

In accordance with the embodiments shown in the drawings, the present invention will be explained below.

First embodiment

Figure 2:
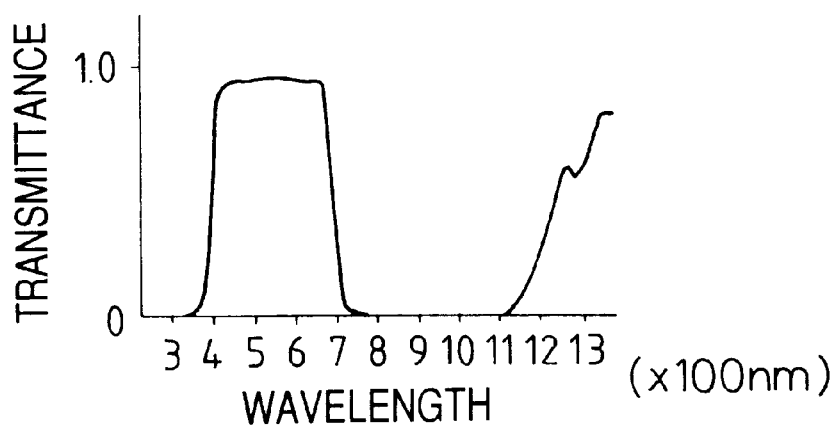
FIG. 2 is a diagram showing an example of the spectral transmittance characteristic of an infrared removing filter used in the first embodiment.

FIG. 1 shows the arrangement of the first embodiment of the light source optical system for endoscopes according to the present invention. FIG. 2 shows an example of the spectral transmittance characteristic of an infrared removing filter used in the first embodiment. In FIG. 1, reference numeral 1 denotes a light-emitting section of a lamp; 2, an elliptical condensing mirror having two focal points, a primary focal point $F_1$ and a secondary focal point $F_2$; 3, a spherical mirror; 4, a relay optical system including two or more lens units, for example, a pair of plano-convex lenses 4a and 4b; 5, an infrared removing filter removably disposed between the pair of plano-convex lenses 4a and 4b; and 6, a stop interposed between the relay optical system 4 and a light guide LG. Since the light-emitting section 1 is situated at the primary focal point $F_1$ of the elliptical condensing mirror 2, light from the light-emitting section 1 is reflected and condensed by the elliptical condensing mirror 2 and forms the bright spot image of the light-emitting section 1 at the secondary focal point $F_2$. The light of this image is further condensed on the entrance end face of the light guide LG by the relay optical system 4. The spherical mirror 3, which lies on the same spherical surface, is located so that its center of curvature is practically coincide with the primary focal point $F_1$ of the elliptical condensing mirror 2 in order that rays emitted from the light emitting section 1 and escaping forward through the aperture of the elliptical condensing mirror 2 are reflected back to the position of the light-emitting section 1.

The elliptical condensing mirror 2 in the present invention satisfies Eq. (1) already mentioned. Moreover, it is desirable that the elliptical condensing mirror 2 satisfies the following conditions:

$$1.9 < F/X < 8.0 \quad (1')$$

$$0.09 < F/\phi < 1.35 \quad (1'')$$

where X is the size of the light-emitting section 1 of the lamp along the optical axis and $\phi$ is the aperture diameter of the elliptical condensing mirror 2.

Since the first embodiment is constructed with the elliptical condensing mirror 2 satisfying Eq. (1), the light emitted from the light-emitting section 1 of a certain size can be efficiently condensed at the entrance end of the light guide LG, and the entire light source optical system can be designed to be compact. Specifically, if the focal length F of the elliptical condensing mirror 2 is set below the lower limit of Eq. (1), the major axis of the ellipse becomes relatively long compared with the minor axis to make a large difference in curvature between different portions of the ellipse. In this way, rays of light originating from a point shifted from the primary focal point $F_1$ will be collected at a position considerably shifted from the secondary focal point $F_2$. Consequently, the projected image of the light-emitting section 1 is markedly distorted, and rays capable of being incident through the relay optical system 4 on the entrance end face of the light guide LG are limited to those emitted from a part of the light-emitting section. On the other hand, if the focal length F exceeds the upper limit of Eq. (1), there will be little difference in length between the major and minor axes of the ellipse and the curvature of the ellipse becomes moderate. When such an ellipse is used for the elliptical condensing mirror, the aperture diameter of the elliptical condensing mirror 2 must be enlarged in order to efficiently condense the light emitted from the light-emitting section 1, and thus compactness of the light source optical system cannot be maintained.

Furthermore, the elliptical condensing mirror 2 satisfies Eqs. (1') and (1''). Eq. (1') defines the condition that the projected image of the light-emitting section 1 formed by the elliptical condensing mirror 2 is not distorted with respect to the size X of the light-emitting section 1 along the optical axis. If the lamp is combined with the elliptical condensing mirror 2 so that the value of F/X is set below the lower limit of Eq. (1'), the projected image of the light-emitting section 1 by the elliptical condensing mirror 2 will be distorted and the efficiency of incidence of light on the entrance end face of the light guide LG will be impaired. This indicates that, for example, when the size X of the light-emitting section, along the optical axis, of the lamp, which is located close to the primary focal point of the elliptical condensing mirror with a certain focal length, is such as to exceed the lower limit of Eq. (1'), rays emitted from such a portion as to exceed the lower limit of Eq. (1'), of the light-emitting section, are collected at a position considerably shifted from the secondary focal point of the elliptical condensing mirror 2. As a result, the projected image of the light-emitting section is distorted. Conversely, if the lamp is combined with the elliptical condensing mirror 2 so that the value of F/X is set beyond the upper limit of Eq. (1'), the elliptical condensing mirror becomes much larger than is necessary and compactness of the light source optical system cannot be held.

Eq. (1'') defines the condition for determining an effective diameter most suitable for the elliptical condensing mirror with the focal length determined by Eq. (1'). Specifically, in view of the relationship between the angle of incidence of a ray on the entrance end face of the light guide LG and the numerical aperture of the light guide, if the effective diameter $\phi$ of the elliptical condensing mirror becomes so large as to pass the lower limit of Eq. (1'') with respect to the focal length F of the elliptical condensing mirror 2, the angle of incidence of the ray on the entrance end face of the light guide LG becomes larger than that corresponding to the numerical aperture of the light guide. Thus, the area of the elliptical condensing mirror reflecting rays which cannot be substantially transmitted by the light guide is merely added and the amount of light incident on the light guide is not increased, with the result that only the elliptical condensing mirror becomes large-sized. On the other hand, if the effective diameter $\phi$ of the elliptical condensing mirror becomes so small as to exceed the upper limit of Eq. (1''), the area of the elliptical condensing mirror reflecting rays at the angles of incidence at which the rays can be substantially transmitted by the light guide will be eliminated and the amount of light incident on the light guide will be decreased.

In the elliptical condensing mirror 2 of the first embodiment, as mentioned above, the focal length of the elliptical condensing mirror 2 is determined with respect to the light-emitting section having a certain size along the optical axis in such a way as to satisfy Eq. (1') as well as Eq. (1). Furthermore, the effective diameter is determined in such a way as to satisfy Eq. (1'') with respect to the elliptical condensing mirror, and thereby the amount of light incident on the light guide and the size of the elliptical condensing mirror can be optimized. Also, the values of respective parameters relative to the elliptical condensing mirror 2 of the first embodiment are as shown in Table 1.

TABLE 1

| X (mm) | α (mm) | β (mm) | φ (mm) | F (mm) | F/X | F/φ |
|---|---|---|---|---|---|---|
| 3.0 | 35.8 | 28.4 | 50.0 | 11.3 | 3.77 | 0.23 |

The relay optical system 4 is composed of at least two lens units, each having a positive refracting power, and has the function of transmitting the image of the light-emitting section 1 projected by the elliptical condensing mirror 2 to the entrance end face of the light guide LG. The first embodiment is constructed so that rays incident on the relay optical system 4 are converted into a parallel beam by the first plano-convex lens 4a with the positive refracting power and the beam is condensed on the entrance end face of the light guide by the second plano-convex lens 4b. The convex side of each of the plano-convex lenses 4a and 4b is configured as an aspherical surface whose curvature reduces progressively in separating from the axis of the optical system. This makes it possible to correct for axial aberration produced in the relay optical system 4 and obviate the defect that the efficiency of incidence of rays on the light guide LG is impaired by the distortion of the image of the lightemitting section 1 transmitted to the entrance end face of the light guide LG. When f denotes the focal length of the lens unit located closest to the light guide LG, of the lens units constituting the relay optical system 4, namely that of the plano-convex lens 4b, and D denotes the diameter of the axial light beam incident on the lens unit, the relay optical system 4 is designed to satisfy the following condition:

$$0.556 < |f/D| < 1.462 \quad (1''')$$

The relay magnification of the relay optical system 4 used in the present invention is governed by the focal length of the lens unit located closest to the light guide LG. In order to determine the focal length of the lens unit, that is, the relay magnification of the relay optical system 4, it is desirable that the efficiency of incidence of the ray on the light guide LG is optimized in view of the relationship between the angle of incidence of the ray on the entrance end face of the light guide LG and the numerical aperture of the light guide LG. Eq. (1''') defines the condition for determining the relay magnification so that the ray is efficiently incident on the light guide.

In the first embodiment, if the value of $|f/D|$ is below the lower limit of Eq. (1''') in the relay optical system 4, a ray with the angle of incidence larger than that corresponding to the numerical aperture of the light guide will be produced, and the efficiency of use of the amount of light will be impaired. Conversely, if the value of $|f/D|$ exceeds the upper limit of Eq. (1'''), the image of the light-emitting section transmitted to the entrance end face of the light guide will be enlarged, and similarly the efficiency of use of the amount of light will be impaired. In the first embodiment, the light source optical system is thus designed to satisfy Eqs. (1)-(1''') with respect to the elliptical condensing mirror 2 and the relay optical system 4. In this way, even when the light-emitting section has a certain length along the optical axis as in the discharge lamp, axial light is efficiently collected and rendered incident on the entrance end face of a relatively fine light guide for endoscopes and can be transmitted to the exit end side thereof, and the entire optical system can be constructed to be compact.

According to the first embodiment, since the infrared removing filter 5 is used at a place where the light beam is parallel with the optical axis, the effect of the filter 5 for removing infrared rays can be optimized, and the entrance end face of the light guide LG can be positively protected from burning damage caused by infrared rays.

Also, in the first embodiment, when an infrared cutoff coating, instead of the infrared removing filter 5, is applied to the flat side of at least one of the plano-convex lenses 4a and 4b, the same effect can be achieved, and thereby the entire optical system can be designed to be more compact.

Second embodiment

Figure 3:
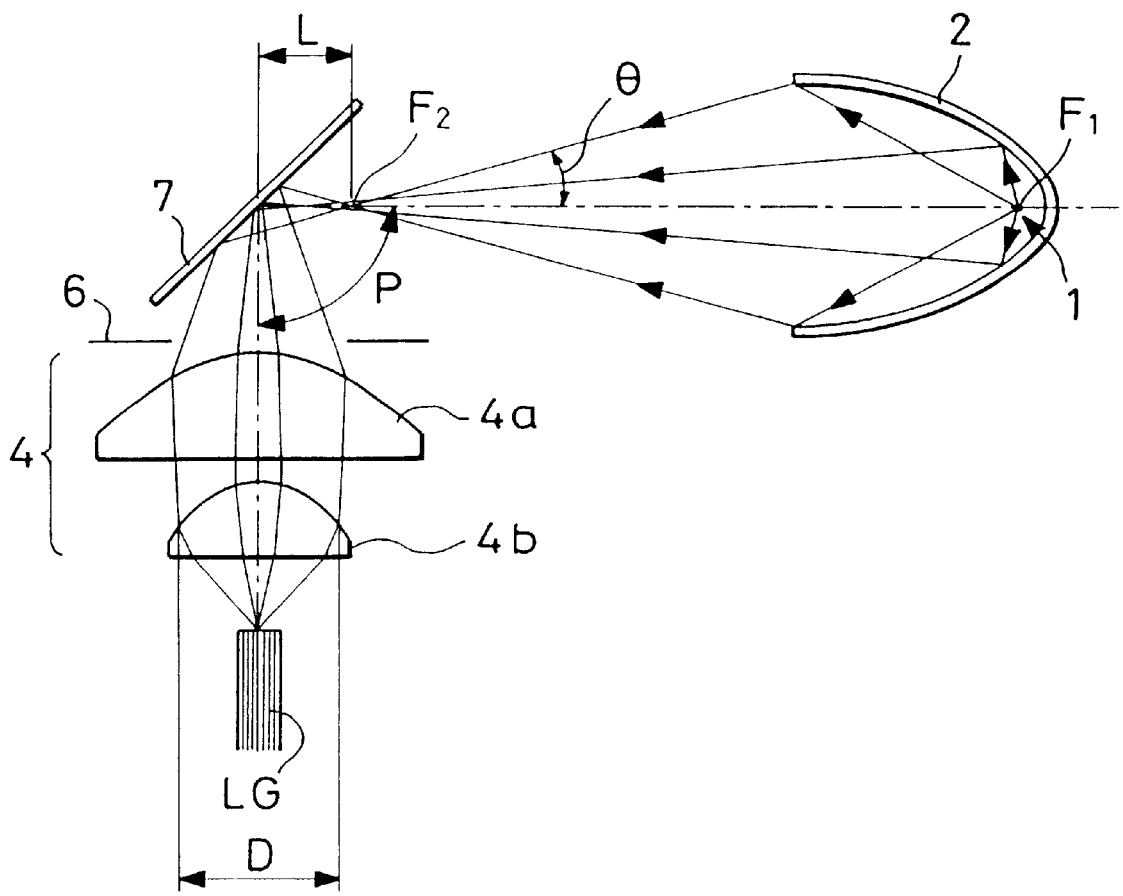
FIG. 3 is a view showing the arrangement of a second embodiment of the light source optical system for endoscopes according to the present invention.

FIG. 3 shows the arrangement of the second embodiment of the light source optical system for endoscopes according to the present invention. In this figure, like numerals and symbols are used in like or similar members with reference to the first embodiment. The second embodiment has the same arrangement as the first embodiment with the exception that a plane mirror 7 is interposed on the optical path between the elliptical condensing mirror 2 and the relay optical system 4 so that the optical path is bent at right angles, and the stop 6 is placed on the entrance side of the relay optical system 4.

In the second embodiment, the light source optical system satisfies Eqs. (2) and (3) previously mentioned. Specifically, in these equations, P denotes an angle between the optical axis of the light beam which travels from the light-emitting section 1 to the plane mirror 7 and the optical axis of the light beam which travels from the plane mirror 7, through the relay optical system 4, to the entrance end face of the light guide LG; L denotes a distance from the secondary focal point $F_2$ of the elliptical condensing mirror 2 to the plane mirror 7; and θ denotes the maximum angle of incidence of a ray reflected by the elliptical condensing mirror 2 on the secondary focal point $F_2$.

Eq. (2) defines the angle at which the optical path of the light source optical system is bent by the plane mirror 7, while Eq. (3) specifies the location of the plane mirror 7 in the light source optical system.

In this case, if the angle P is smaller than the value of the lower limit of Eq. (2), a positional problem will arise that the relay optical system 4 may penetrate into the light beam reaching the plane mirror 7 from the elliptical condensing mirror 2 to block a part of the light beam. On the other hand, if the angle P becomes larger than the value of the upper limit of Eq. (2), the problem will be raised that the optical system occupies a comparatively large space and compactness of the optical system cannot be achieved. Further, if the value of $|L/\tan \theta|$ is beyond the limit of Eq. (3), the section of the light beam will be increased and the optical system must be enlarged. The result is that the compactness cannot be achieved.

In this way, the plane mirror 7 is placed in the light source optical system so as to satisfy Eqs. (2) and (3) and bends the optical path, and thereby a space for incorporating the light source optical system can be made extremely small. In the second embodiment, the elliptical condensing mirror 2 and the relay optical system 4 are designed as in the first embodiment, and the plane mirror 7 is placed in the light source optical system so as to satisfy Eqs. (2) and (3) and bends the optical path at right angles. Hence, even when the light-emitting section has a certain length along the optical axis as in the discharge lamp, source light can be efficiently condensed and rendered incident on the entrance end face of a relatively fine light guide for endoscopes and can be transmitted to the exit end side. Moreover, the second embodiment, in contrast with the first embodiment, is capable of constructing a further compact light source optical system. Also, the values of respective parameters relative to the elliptical condensing mirror 2 of the second embodiment are as shown in Table 2.

TABLE 2

| X (mm) | α (mm) | β (mm) | φ (mm) | F (mm) | F/X | F/φ |
|---|---|---|---|---|---|---|
| 0.64 | 33.0 | 13.0 | 25.0 | 2.6 | 4.08 | 0.10 |

Figure 4:
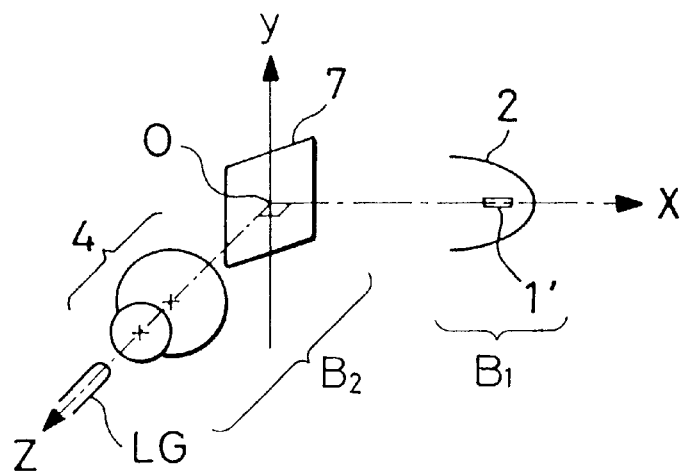
FIG. 4 is a perspective view schematically showing an example where the second embodiment is used.

FIG. 4 shows an example where the light source optical system for endoscopes of the second embodiment is used. According to this example, the elliptical condensing mirror 2 and a discharge lamp 1' are integrally incorporated in a block $B_1$, and the plane mirror 7 and the relay optical system 4 are integrally incorporated in a block $B_2$. The block $B_2$ is designed to be rotatable around an optical axis x of the elliptical condensing mirror 2 or an axis parallel with the optical axis x, for example, around the optical axis x, with a point of intersection 0 of x, y, and z axes in FIG. 4 as a center, thereby facilitating the use of a light source apparatus for endoscopes.

Figure 5:
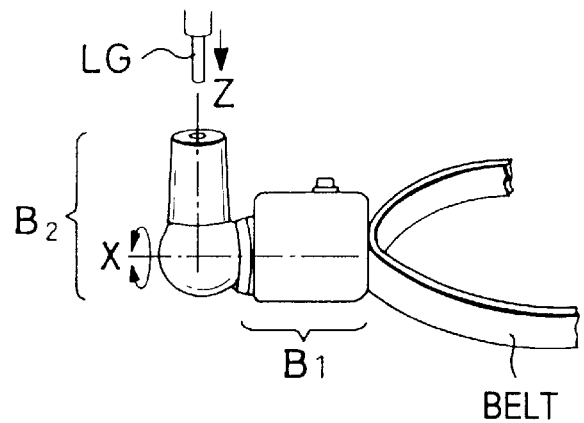
FIG. 5 is a view showing the appearance of a light source apparatus for endoscopes incorporating a light source optical system for endoscopes in FIG. 4.

FIG. 5 shows the appearance of the light source apparatus, in which a belt is used to be portable. In observation through an endoscope, cases frequently occur in which the endoscope must be inserted in a fine curved tube as in the inspection of the inner wall of the tube. In such cases, an observer repeats such behavior as to bend the endoscope or vary his position so that the endoscope can be easily inserted in the fine tube. In a conventional light source apparatus for endoscopes, since a connection with a light guide connector is fixed, a light guide cable is twisted and the observer's work efficiency is considerably impaired. This is responsible for undue fatigue of the observer. According to the example where the light source optical system of the second embodiment is used, the block $B_2$ is designed to be rotatable around the optical axis x, with the point of intersection 0 of x, y, and z axes in FIG. 4 as a center, and hence the direction of the light guide connector can be changed in such a way that the light guide LG is not twisted. Thus, the second embodiment has the great advantage that the observer can easily insert the endoscope without assuming an uncomfortable position. Moreover, if the block $B_2$ is made rotatable not only around the optical axis x but also around the y and z axes, with the point of intersection 0 as a center, to such an extent that the plane mirror does not block the light beam, the facilitation of use of the apparatus will be further improved.

Figure 6:
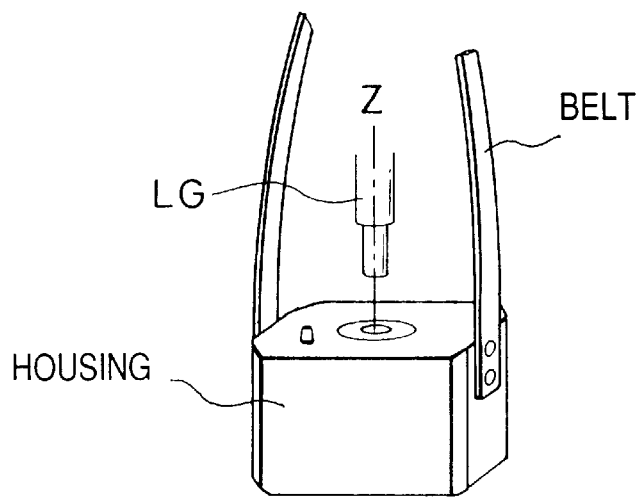
FIG. 6 is a view showing the appearance of another example of the light source apparatus for endoscopes.
Figure 7:
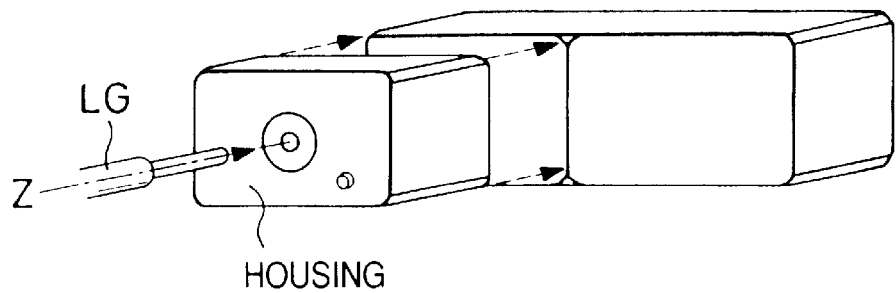
FIG. 7 is a view showing the appearance of still another example of the light source apparatus for endoscopes.

The appearances of the light source apparatuses for endoscopes in which the elliptical condensing mirror 2, the plane mirror 7, and the relay optical system 4 are fixedly arranged in a state where the optical axis x makes a right angle with the z axis are shown in FIG. 6 (shoulder belt type) and FIG. 7 (a type that the light source optical system can be incorporated in a housing rack for endoscopes). The light source optical system of the second embodiment, because its housing space can thus be made very small, is used as a portable light source apparatus integrated with a battery as depicted in FIG. 6, or as a systematic light source incorporated, together with a video system, in the housing rack as depicted in FIG. 7. In this way, a light source apparatus for endoscopes which has exceptional versatility can be designed.

Third embodiment

Figure 8:
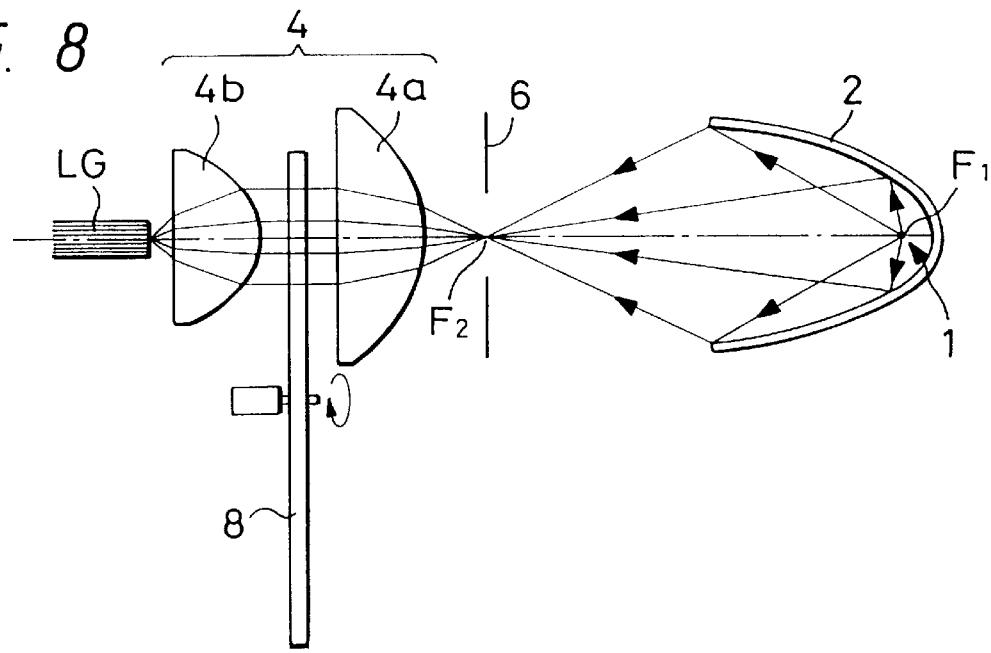
FIG. 8 is a view showing the arrangement of a third embodiment of the light source optical system for endoscopes according to the present invention.
Figure 9A:
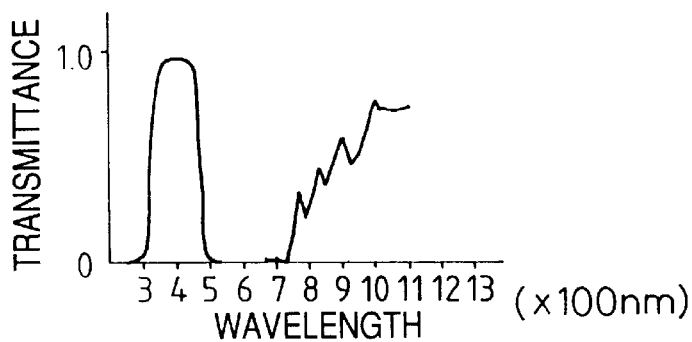
FIGS. 9A, 9B, and 9C are diagrams showing spectral transmittance characteristics of an RGB rotary filter used in the third embodiment.
Figure 9B:
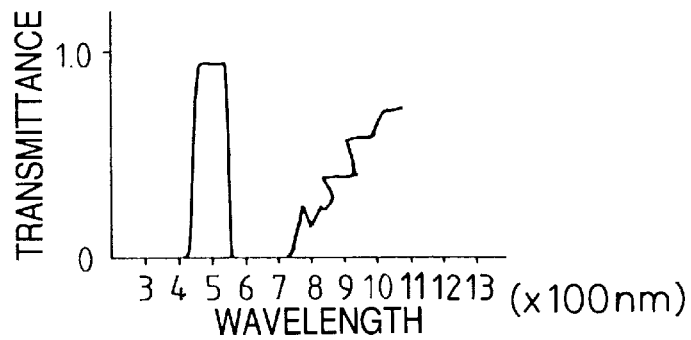
Figure 9C:
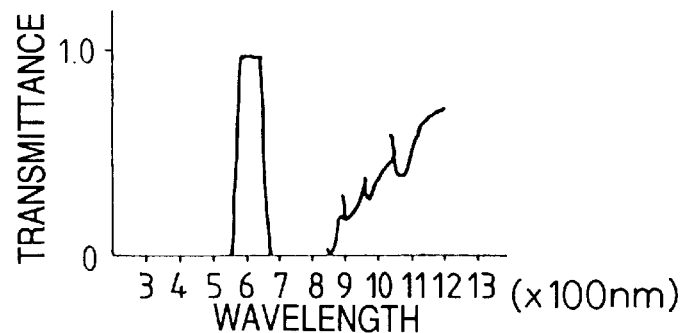

FIG. 8 shows the arrangement of the third embodiment of the light source optical system for endoscopes according to the present invention. FIGS. 9A, 9B, and 9C show the diagrams of spectral transmittance characteristics of an RGB rotary filter used in the third embodiment. In FIG. 8, like numerals and symbols are used in like or similar members with reference to the first embodiment. The third embodiment has the same arrangement as the first embodiment with the exception that the stop 6 is located at the position of the secondary focal point $F_2$ of the elliptical condensing mirror 2, and an RGB rotary filter 8 is used instead of the infrared removing filter 5. The RGB rotary filter 8 comprises a B (blue light) transmission filter, a G (green light) transmission filter, and an R (red light) transmission filter, arranged to be concentric and equidistant, having spectral transmittance characteristics such as those shown in FIGS. 9A, 9B, and 9C, respectively, so that an object to be observed can be viewed as a colored image. Since the fundamental function and effect of the third embodiment are the same as those of the first embodiment, their detailed explanation is omitted. Also, the values of respective parameters relative to the elliptical condensing mirror 2 of the third embodiment are as shown in Table 3.

TABLE 3

| X (mm) | α (mm) | β (mm) | φ (mm) | F (mm) | F/X | F/φ |
|---|---|---|---|---|---|---|
| 1.50 | 50.0 | 33.6 | 66.0 | 11.3 | 7.52 | 0.17 |

What is claimed is:

1. A light source optical system for endoscopes, comprising:

an elliptical condensing mirror for projecting a bright spot of a light-emitting section of a lamp; and a relay optical system for transmitting a projected image of the bright spot to an entrance end face of a light guide;

said elliptical condensing mirror satisfying the following condition:

$$2.0 \text{ mm} < F < 16.0 \text{ mm}$$

where F is a focal length of said elliptical condensing mirror, which is expressed by $F=\beta^2/(2\alpha)$ where (a major axis of an ellipse)/2=α and (a minor axis of the ellipse)/2=β.

2. A light source optical system for endoscopes according to claim 1, wherein a plane mirror is interposed on an optical path between said elliptical condensing mirror and said relay optical system so that said optical path is bent at an angle P satisfying the following condition:

$$30° < P < 120°$$

3. A light source optical system for endoscopes according to claim 2, wherein said plane mirror is located so as to satisfy the following condition:

$$|L/\tan \theta| \leq 5.5$$

where L is a distance from a secondary focal point of said elliptical condensing mirror to said plane mirror and θ is a maximum angle of incidence of a ray reflected by said elliptical condensing mirror on the secondary focal point.

4. A light source optical system for endoscopes according to claims 1 or 3, wherein said relay optical system includes at least two lens units, each having a positive refracting power.

5. A light source optical system for endoscopes according to claim 4, wherein said relay optical system satisfies the following condition:

$$0.556 < |f/D| < 1.462$$

where f is a focal length of a lens unit located closest to said light guide, of lens units constituting said relay optical system and D is a diameter of an axial light beam incident on said lens unit.

6. A light source optical system for endoscopes according to claim 5, wherein said relay optical system includes at least one aspherical surface whose curvature reduces progressively in separating from an optical axis of said relay optical system.

7. A light source optical system for endoscopes according to claim 6, wherein each of lens units constituting said relay optical system is a plano-convex lens in which one surface is convex and a remaining surface is flat.

8. A light source optical system for endoscopes according to claim 7, wherein an infrared cutoff coating is applied to a flat side of said plano-convex lens.

9. A light source optical system for endoscopes according to claim 5, wherein a filter is removably disposed in said relay optical system.

10. A light source optical system for endoscopes according to claim 3, wherein said elliptical condensing mirror and said lamp are integrally constructed, and said plane mirror and said relay optical system are integrally constructed to be rotatable around one of an optical axis of said lamp and an axis parallel with said optical axis.

11. A light source optical system for endoscopes according to claim 9, wherein said filter is an RGB rotary filter.

12. A light source optical system for endoscopes according to claim 9, wherein said elliptical condensing mirror satisfies the following conditions:

$$1.9 < F/X < 8.0$$

$$0.09 < F/\phi < 0.35$$

where F is a focal length of said elliptical condensing mirror, X is a size of the light-emitting section of said lamp along an optical axis, and $\phi$ is an aperture diameter of said elliptical condensing mirror.

13. A light source optical system for endoscopes according to claim 12, wherein a spherical mirror having a center of curvature, close to a primary focal point of said elliptical condensing mirror, is placed opposite to said elliptical condensing mirror.

14. A light source optical system for endoscopes according to claim 10, wherein said elliptical condensing mirror satisfies the following conditions:

$$1.9 < F/X < 8.0$$

$$0.09 < F/\phi < 0.35$$

where F is a focal length of said elliptical condensing mirror, X is a size of the light-emitting section of said lamp along an optical axis, and $\phi$ is an aperture diameter of said elliptical condensing mirror.

* * * * *